(12) United States Patent
Zheng et al.

(10) Patent No.: US 11,562,830 B2
(45) Date of Patent: Jan. 24, 2023

(54) MERCHANT EVALUATION METHOD AND SYSTEM

(71) Applicant: Advanced New Technologies Co., Ltd., Grand Cayman (KY)

(72) Inventors: Lin Zheng, Zhejiang (CN); Jiang Zhu, Zhejiang (CN); Jie Li, Zhejiang (CN); Tao Chen, Zhejiang (CN); Tianyi Zhang, Zhejiang (CN)

(73) Assignee: Advanced New Technologies Co., Ltd., Grand Cayman (KY)

( * ) Notice: Subject to any disclaimer, the term of this patent is extended or adjusted under 35 U.S.C. 154(b) by 411 days.

(21) Appl. No.: 16/661,457

(22) Filed: Oct. 23, 2019

(65) Prior Publication Data

US 2020/0058406 A1    Feb. 20, 2020

Related U.S. Application Data

(63) Continuation of application No. PCT/CN2018/097340, filed on Jul. 27, 2018.

(30) Foreign Application Priority Data

Jul. 28, 2017 (CN) .......................... 201710631485.8

(51) Int. Cl.
*G16H 50/30* (2018.01)
*G06Q 10/06* (2012.01)
(Continued)

(52) U.S. Cl.
CPC ....... *G16H 50/30* (2018.01); *G06Q 10/06393* (2013.01); *G06Q 20/351* (2013.01);
(Continued)

(58) Field of Classification Search
CPC ....... G16H 50/00–80; G06Q 10/00–30; G06Q 20/00–425; G06Q 30/00–08; G06Q 50/00–34
See application file for complete search history.

(56) References Cited

U.S. PATENT DOCUMENTS 7,290,212 B2 * 10/2007 Fushimi ................ G06T 11/206
382/113
10,853,739 B2 * 12/2020 Truong .................. G06N 20/00
(Continued)

FOREIGN PATENT DOCUMENTS

CN       105608600 A    5/2016
CN       105869001 A    8/2016
(Continued)

OTHER PUBLICATIONS

Singh et al., A Review of Supervised Machine Learning Algorithms, 2016, IEEE (Year: 2016).*
(Continued)

*Primary Examiner* — John W Hayes
*Assistant Examiner* — Chenyuh Kuo
(74) *Attorney, Agent, or Firm* — Finnegan, Henderson, Farabow, Garrett & Dunner, LLP

(57) ABSTRACT

A merchant evaluation method includes: acquiring multi-dimensional evaluation index data of a merchant to be evaluated; for the multi-dimensional evaluation index data, obtaining, by calculation based on standard normal distribution, a health portrait of the merchant to be evaluated, and obtaining, by calculation based on a geometric mean, a health score of the merchant to be evaluated, wherein the health portrait is data representing at least one evaluation result of the merchant to be evaluated; and outputting the health portrait and the health score of the merchant to be evaluated.

9 Claims, 7 Drawing Sheets

(51) Int. Cl.
*G06Q 20/34* (2012.01)
*G06Q 20/40* (2012.01)
*G06Q 30/02* (2012.01)
*G06Q 30/06* (2012.01)
*G06Q 50/22* (2018.01)

(52) U.S. Cl.
CPC ..... *G06Q 20/4016* (2013.01); *G06Q 30/0201* (2013.01); *G06Q 30/06* (2013.01); *G06Q 30/0609* (2013.01); *G06Q 50/22* (2013.01)

(56) References Cited

U.S. PATENT DOCUMENTS

| | | | |
|---|---|---|---|
| 11,030,535 B1* | 6/2021 | Arora | G06N 5/04 |
| 2006/0101048 A1* | 5/2006 | Mazzagatti | G06F 16/2246 |
| 2008/0270209 A1* | 10/2008 | Mauseth | G06Q 30/0201 |
| | | | 705/7.29 |
| 2009/0048884 A1* | 2/2009 | Olives | G06Q 40/12 |
| | | | 705/7.33 |
| 2010/0274787 A1* | 10/2010 | Lu | G06F 16/355 |
| | | | 707/737 |
| 2011/0093324 A1* | 4/2011 | Fordyce, III | G06Q 30/0226 |
| | | | 705/14.27 |
| 2014/0108072 A1* | 4/2014 | McGowan | G06Q 10/0637 |
| | | | 705/7.11 |
| 2015/0363840 A1* | 12/2015 | Gupta | G06Q 30/0282 |
| | | | 705/347 |
| 2016/0110812 A1* | 4/2016 | Mun | G06Q 40/06 |
| | | | 705/36 R |

FOREIGN PATENT DOCUMENTS

| | | | |
|---|---|---|---|
| JP | 2007058756 A * | 3/2007 | |
| JP | 2007058756 A | 3/2007 | |
| JP | 2013084208 A | 5/2013 | |
| JP | 2016512909 A | 5/2016 | |
| KR | 20020007140 A | 1/2002 | |
| KR | 100776187 B1 | 11/2007 | |
| KR | 20070108318 A | 11/2007 | |

OTHER PUBLICATIONS

Guan et al. Weakly-Supervised Deep Learning for Customer Review Sentiment Classification, IJCAI, 2016 (Year: 2016).*
International Search Report for International Application No. PCT/CN2018/097340, dated Oct. 18, 2018.
Extended European Search Report in the European Application No. 18837166.0 dated Mar. 2, 2020.
Decision of Rejection of Japanese Application No. 2019-556957, dated Sep. 7, 2021.
Decision of Patent Grant of Korean Application No. 10-2019-7031838, dated Nov. 17, 2021.
Examination Report of Indian Application No. 201937041076, dated Jul. 12, 2021.
Office Communication in European Application No. 18 837 166.0, dated Sep. 16, 2021.
Notice of Eligibility for Grant of Singapore Application No. 11201909476Q, dated Aug. 19, 2021.
Examination Report for European Application No. 18837166.0, dated Dec. 23, 2020.
Written Opinion for Application No. 11201909476Q, issued by the Intellectual Property Office of Singapore, dated Oct. 5, 2020.
Notice of Reasons for Rejection of Japanese Application No. 2019-556957, dated Apr. 2, 2021.
Notice of Preliminary Rejection of Korean Application No. 10-2019-7031838, dated May 6, 2021.
Takada, N., "New Techniques for Interpreting and Applying the Results of Logistic Regression Analysis—an Example of the credit risk scoring model", Provision, IBM Japan, Ltd., May 9, 2007, No. 53, vol. 14, No. 2, Spring 2007, pp. 71-77.
Yamazaki, Y., "Introduction to Establishment of 'Business Model,'" Chukei Shuppan, Nov. 3, 2000, 1st edition, pp. 132-135.
Office Action in Indonesian Application No. P00201909158, dated Sep. 23, 2022.
Decision to Refuse a European Patent application in European Application No. 18 837 166.0, dated Apr. 1, 2022.

* cited by examiner

MERCHANT EVALUATION METHOD AND SYSTEM

CROSS-REFERENCE TO RELATED APPLICATIONS

This application is a continuation application of International Application No. PCT/CN2018/097340, filed on Jul. 27, 2018, which is based upon and claims priority to Chinese Patent Application No. 201710631485.8, filed on Jul. 28, 2017, the entire content of all of which is incorporated herein by reference.

TECHNICAL FIELD

The present specification relates to the field of Internet technologies, and in particular to a merchant evaluation method and system.

TECHNICAL BACKGROUND

With the popularization of smart terminals, users are more and more relying on e-commerce for shopping without going out. In order to improve user satisfaction, to avoid fake commodities as much as possible, and to ensure the safe operation of e-commerce platforms, it is crucial for e-commerce to select and certify merchants. Therefore, there is a need for evaluating merchants to provide a basis for the certification of the merchants.

SUMMARY

Embodiments of the specification provide a merchant evaluation method and system.

In a first aspect, a merchant evaluation method includes: acquiring multi-dimensional evaluation index data of a merchant to be evaluated; for the multi-dimensional evaluation index data, obtaining, by calculation based on standard normal distribution, a health portrait of the merchant to be evaluated, and obtaining, by calculation based on a geometric mean, a health score of the merchant to be evaluated, wherein the health portrait is data representing at least one evaluation result of the merchant to be evaluated; and outputting the health portrait and the health score of the merchant to be evaluated.

In a second aspect, a merchant evaluation system includes: a processor; and a memory storing instructions executable by the processor; wherein the processor is configured to: acquire multi-dimensional evaluation index data of a merchant to be evaluated; for the multi-dimensional evaluation index data, obtain, by calculation based on standard normal distribution, a health portrait of the merchant to be evaluated, and obtain, by calculation based on a geometric mean, a health score of the merchant to be evaluated; and output the health portrait and the health score of the merchant to be evaluated.

In a third aspect, a non-transitory computer-readable storage medium has stored therein instructions that, when executed by a processor of a device, cause the device to perform a merchant evaluation method. The method includes: acquiring multi-dimensional evaluation index data of a merchant to be evaluated; for the multi-dimensional evaluation index data, obtaining, by calculation based on standard normal distribution, a health portrait of the merchant to be evaluated, and obtaining, by calculation based on a geometric mean, a health score of the merchant to be evaluated, wherein the health portrait is data representing at least one evaluation result of the merchant to be evaluated; and outputting the health portrait and the health score of the merchant to be evaluated.

The beneficial effects of the embodiments of the specification are as follows. Firstly, by setting evaluation indexes in multiple dimensions, all-round evaluation can be conducted on a merchant to be evaluated; secondly, starting from data analysis, for example, obtaining, by calculation based on standard normal distribution, a health portrait of the merchant to be evaluated and obtaining, by calculation based on a geometric mean, a health score of the merchant to be evaluated, the driving effect on data is strengthened and the human experience is weakened, making the evaluation results more credible. In addition, by not only providing the health score but also providing the health portrait, the health conditions of each evaluation index can be more intuitively viewed, and moreover, because the evaluation is conducted based on the merchant historical data (e.g., a black sample and a white sample), data distribution of the merchant to be evaluated among history merchants can be reflected, and the health of the merchant can be measured according to the merchant's position in the score distribution.

DETAILED DESCRIPTION

Detailed description is made below for embodiments of the specification through the accompanying drawings. It should be understood that the embodiments of the specification are exemplary, rather than all embodiments consistent with the specification. Embodiments of the specification may also be combined.

Figure 1:
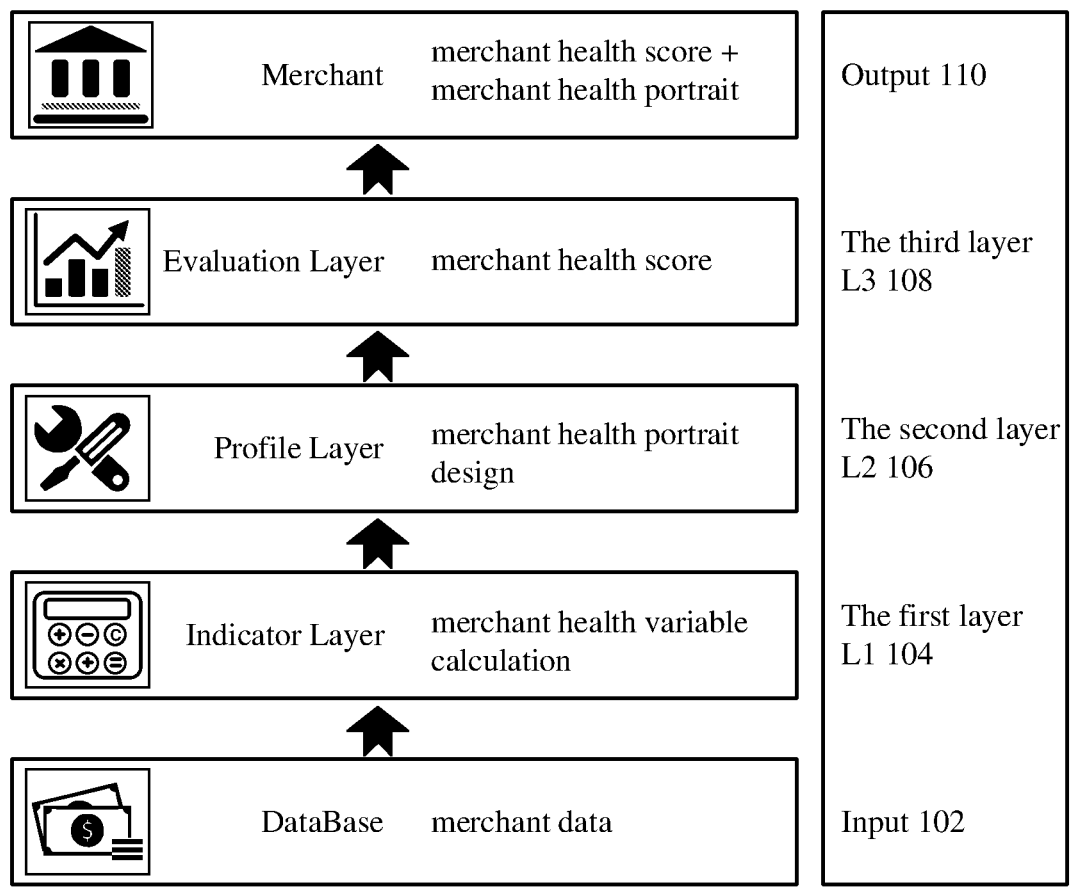
FIG. 1 is a schematic diagram of a merchant evaluation system according to embodiments of the specification.

FIG. 1 is a schematic diagram of a merchant evaluation system 100 according to embodiments of the specification. In general, the merchant evaluation system 100 includes an input 102, a first layer 104, a second layer 106, a third layer 108, and an output 110. The input 102 is configured to input merchant related data, the first layer 104 mainly calculates and processes the merchant related data, the second layer 106 obtains a health portrait of the merchant, the third layer 108 obtains a health score of the merchant, and the output 110 outputs the health portrait of the merchant and the health score of the merchant.

The health portrait of the merchant can be understood as an image intuitively describing the "health conditions" of the merchant. In the embodiment, the health conditions of the merchant are the result of a comprehensive consideration of data of the merchant in various aspects, and are an important basis reflecting the possibility for the merchant to pass the certification. The health conditions can involve many aspects, such as merchant background, operation history, operation capability, business relationship and operation characteristics, etc. The health score of the merchant is a numerical value that is easy to refer to, and the credibility level of the merchant can be determined by a magnitude of the numerical value.

Figure 2:
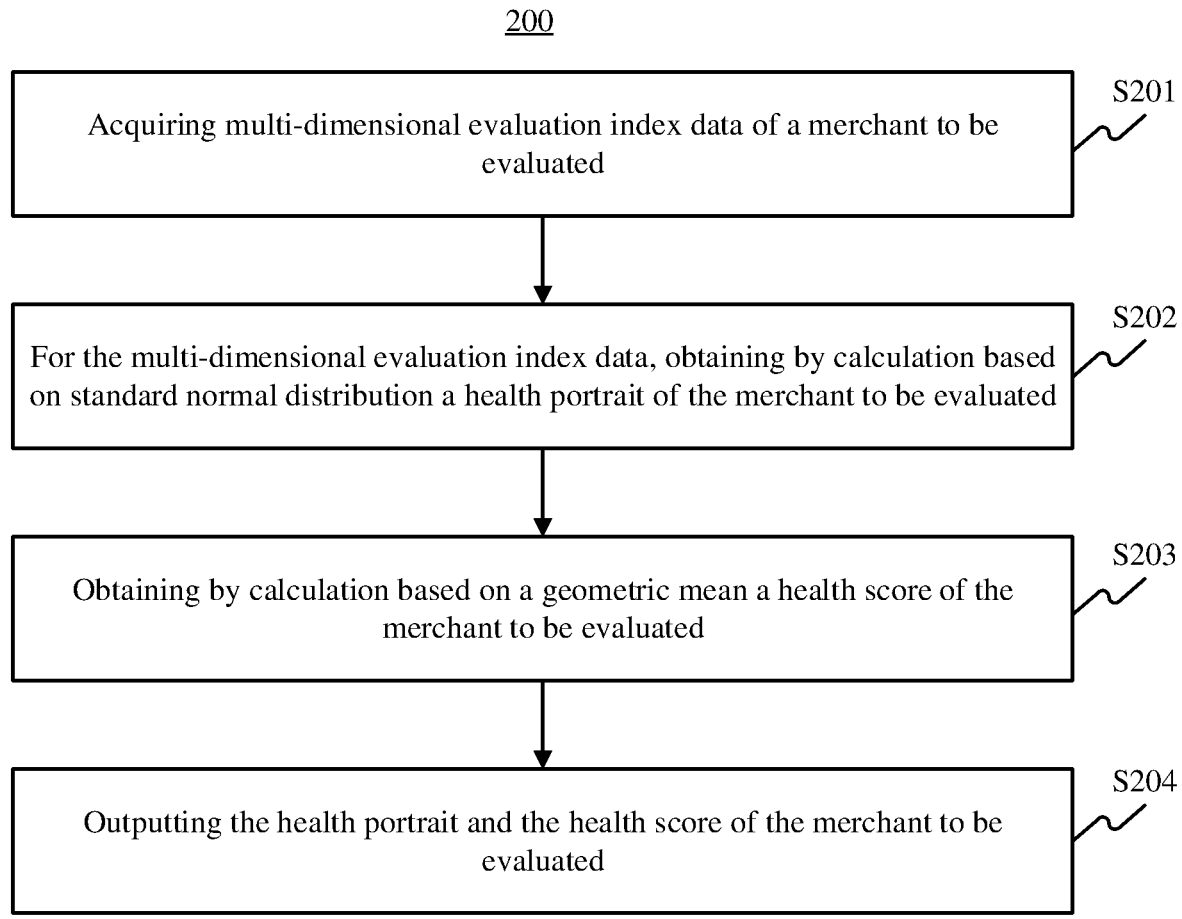
FIG. 2 is a flowchart of a merchant evaluation method according to an embodiment.

FIG. 2 is a flow chart of a merchant evaluation method 200, according to an embodiment. Referring to FIG. 2, the method 200 may include the following steps.

In step S201, multi-dimensional evaluation index data of a merchant to be evaluated is acquired.

In the embodiment, a merchant may be an entity unit engaged in sales business and directly facing external customers, such as merchants of Alipay Koubei and merchants of offline Alipay scan pay. For example, a merchant may be a physical store. In order to conduct all-round evaluation on the merchant, multiple evaluation indexes can be set. It can be appreciated that the more evaluation indexes there are, the more reliable the evaluation result of the merchant becomes. In other words, evaluation indexes in multiple dimensions are set, so as to obtain an evaluation result of higher credibility through analysis and processing of the multi-dimensional index data.

In an embodiment, the multi-dimensional evaluation index data includes any combination of merchant background identity evaluation index data, merchant operation history evaluation index data, merchant operation capability evaluation index data, merchant business relationship evaluation index data and merchant operation characteristics evaluation index data.

In the embodiment, the evaluation index data in each dimension is data obtained from original information used for describing the index and is used to measure the degree of the index. In one implementation, by inputting the original evaluation index description information into an index model preset for the index, the evaluation index data for describing a score of the index is obtained, thereby reflecting the evaluation index data through the score of each index. Taking the merchant background identity index as an example, the original description information of the index includes: a merchant certification level/business license completeness, information about whether the merchant is involved in illegal activities, merchant maturity/value information, etc.; and by inputting these pieces of original description information into the preset index model, a score of the index can be obtained, i.e., obtaining the evaluation index data.

The merchant background identity evaluation index data can be obtained through the merchant background identity description information. The merchant background identity description information can be: a merchant certification level/business license completeness (e.g., whether the merchant qualification is sound, and whether materials such as industrial and commercial record are complete); whether the merchant is involved in illegal activities (e.g., whether the merchant and the natural person behind the merchant have any gang and gray activity); and merchant maturity/value (e.g., whether a merchant is a mature merchant on the platform, and the value of the merchant's account).

The merchant operation history evaluation index data can be obtained through the merchant operation history description information. The merchant operation history description information can be: credible operation accumulation (e.g., historical trading volume of the merchant, the number of users and business hours); historical complaint conditions (e.g., the proportion of transactions involving complaints in the merchant's history); and historical buyer evaluation (e.g., the number of good and bad comments received by the merchant on the platform, and an overall evaluation score).

The merchant operation capability evaluation index data can be obtained through the merchant operation capability description information. The merchant operation capability description information can be: a merchant scale (e.g., the number of stores under the merchant, an average daily amount, and an average daily number of trading users); capital turnover capacity (e.g., difference between income and expenditure of the merchant, liabilities and performance capabilities); and merchant operation advantages (e.g., the amount of year-on-year and chain growth in trading volume of the merchant, and the quantile of the merchant's trading volume among similar merchants).

The merchant business relationship evaluation index data can be obtained through the merchant business relationship description information. The merchant business relationship description information can be: capital relationship (e.g., among the users who have conducted financial transactions with the merchant, the proportion of users involved in illegal activities, and the proportion of high-value users); social relationships (e.g., among social friends of the merchant, the proportion of users involved in illegal activities, and the proportion of high-value users); and merchant contact list (e.g., in the merchant's mobile phone contact list, the proportion of users involved in illegal activities, and the proportion of high-value users).

The merchant operation characteristics evaluation index data can be obtained through the merchant operation characteristics description information. The merchant operation characteristics description information can be: characteristics of buyers under the merchant (e.g., the proportion of new users among the buyers, and the proportion of repurchasing users); risk of the operation content (e.g., the proportion of recently complained keywords in the operation content, and whether an illegal and prohibited keyword is contained); and address/time period stability (e.g., whether the merchant is operating in its usual geographical position, and whether the business hours are stable).

In step S202, for the multi-dimensional evaluation index data, a health portrait of the merchant to be evaluated is obtained by calculation based on standard normal distribution. For example, the health portrait is data representing at least one evaluation result of the merchant to be evaluated.

In Standard Normal Distribution, the expected value $\mu=0$, that is, the normal distribution is denoted as N (0, 1) under the condition that the curve image symmetry axis is the Y axis and the standard deviation $\sigma=1$. In the embodiments of the specification, the historical merchant data is used as the basis for evaluation to calculate the distribution of each index of the merchant to be evaluated in the history of the above-mentioned data, thereby obtaining the health portrait of the merchant to be evaluated. The health portrait reflects the merchant's position in the historical merchant data distribution in an intuitive image from various dimensions.

In step S203, a health score of the merchant to be evaluated is obtained by calculation based on a geometric mean.

In order to avoid uneven distribution of the number of indexes corresponding to each dimension of the health portrait, and to ensure that the final health score of the merchant can respond agilely to an extremely abnormal situation of a certain dimension of the merchant's health portrait, the merchant's health score is obtained not simply by way of direct summation, but by way of taking a geometric mean. The geometric mean is the n-th root of the continued product of n observed values. For example, a geometric mean is taken for probability values of various evaluation indexes of the merchant to be evaluated, to obtain the health score of the merchant to be evaluated.

In step S204, the health portrait and the health score of the merchant to be evaluated are output, e.g., on a screen of an electronic device.

In an embodiment, the evaluation of the merchant can be realized by pre-establishing a merchant evaluation model and inputting data of the merchant to be evaluated into the model.

Accordingly, the merchant evaluation method 200 may further include:

(1) determining evaluation indexes in multiple dimensions, and acquiring a merchant black sample and a merchant white sample; and (2) establishing a logistic regression merchant evaluation model for the evaluation indexes in the multiple dimensions based on the merchant black sample and the merchant white sample, wherein the health portrait and the health score of the merchant to be evaluated are obtained using the merchant evaluation model.

In some embodiments, the logistic regression merchant evaluation model may be a conventional generalized linear model.

In an embodiment, obtaining, by calculation based on standard normal distribution, a health portrait of the merchant to be evaluated includes: inputting the multi-dimensional evaluation index data into the merchant evaluation model, obtaining, by calculation based on standard normal distribution, a probability value of evaluation index data in each dimension, and synthesizing the probability value of the evaluation index data in each dimension to obtain the health portrait of the merchant to be evaluated, wherein the health portrait of the merchant to be evaluated reflects normal distribution of the merchant to be evaluated in merchant evaluation historical data.

In an embodiment, obtaining, by calculation based on a geometric mean, a health score of the merchant to be evaluated includes: obtaining the health score of the merchant to be evaluated, by way of taking an evaluation geometric number of the probability value of the evaluation index data in each dimension of the merchant to be evaluated.

For example, in the process of establishing a merchant evaluation model, by taking a merchant who has been cleared and has been complained and verified in history as a black sample, and a mature merchant without a complaint record as the white sample, a logistic regression model is established using a supervised method in which the black sample and the white sample are respectively used as references, and the weight of each evaluation index is determined, thus obtaining an absolute score of the merchant in each dimension of the health portrait. Moreover, the position, in the score distribution, respectively corresponding to the score in each dimension of the merchant's health portrait is respectively calculated, so as to obtain a relative score.

For example, the merchant is Xi'an Classic Snacks, and scores of five dimensions of the health portrait are obtained according to the logistic regression model. The scores of five dimensions are: background identity 85, operation history 71, operation capability 83, business relationship 90, and operation characteristics 66. From the perspective of overall business, the background identity (average score µ: 72, standard deviation δ: 15) will be converted to standard normal distribution:

$$\frac{x-\mu}{\delta} = \frac{85-72}{15} = 0.86,$$

and according to the standard normal distribution, the corresponding probability value is 0.8501; the operation history (average score µ: 68, standard deviation δ: 30) will be converted to standard normal distribution:

$$\frac{x-\mu}{\delta} = \frac{71-68}{30} = 0.1,$$

and the corresponding probability value is 0.5398; in the same manner, it is respectively calculated that the probability value of the operation capability is 0.8340, the probability value of the business relationship is 0.9535, and the probability value of the operation characteristics is 0.5120. As a result, the health portrait of the merchant Xi'an Classic Snacks is displayed on the screen, such as that shown in FIG. 3. Through the health portrait in FIG. 3, it can be intuitively seen that the three indexes of the merchant's background identity, business relationship and operation capability are in good condition, while the two indexes of the operation characteristics and the operation history are ordinary.

Next, when calculating the health score of the merchant to be evaluated, as described above, in order to avoid uneven distribution of the number of indexes corresponding to the respective dimensions of the health portrait, and to enable that the final health score of the merchant can respond agilely to an extremely abnormal situation in a certain dimension of the merchant's health portrait, the merchant's health score is obtained not simply by way of direct summation, but by way of taking a geometric mean. The specific formula is as follows:

$$G_n = \sqrt[N]{\prod_{i=1}^{n} x_i} = \sqrt[N]{x_1 x_2 x_3 \ldots x_n}.$$

By taking the geometric mean, the unfairness caused by uneven distribution of the number of indexes corresponding to the respective dimensions is avoided.

By way of multiplication, an agile reaction can be made to extremely abnormal behavior in each dimension. For example, if an unlicensed operation of the merchant is detected, the identity background in the health portrait is given 0 point; in the case of summation, a large score may still be output for the merchant due to other indexes, but after taking the geometric mean, a 0 point will also be output.

Still taking the above Xi'an Classic Snacks as an example, the health score of the merchant is calculated as follows:

$$\sqrt[5]{0.8501*0.5398*0.834*0.9535*0.512} = 0.7150.$$

Figure 3:
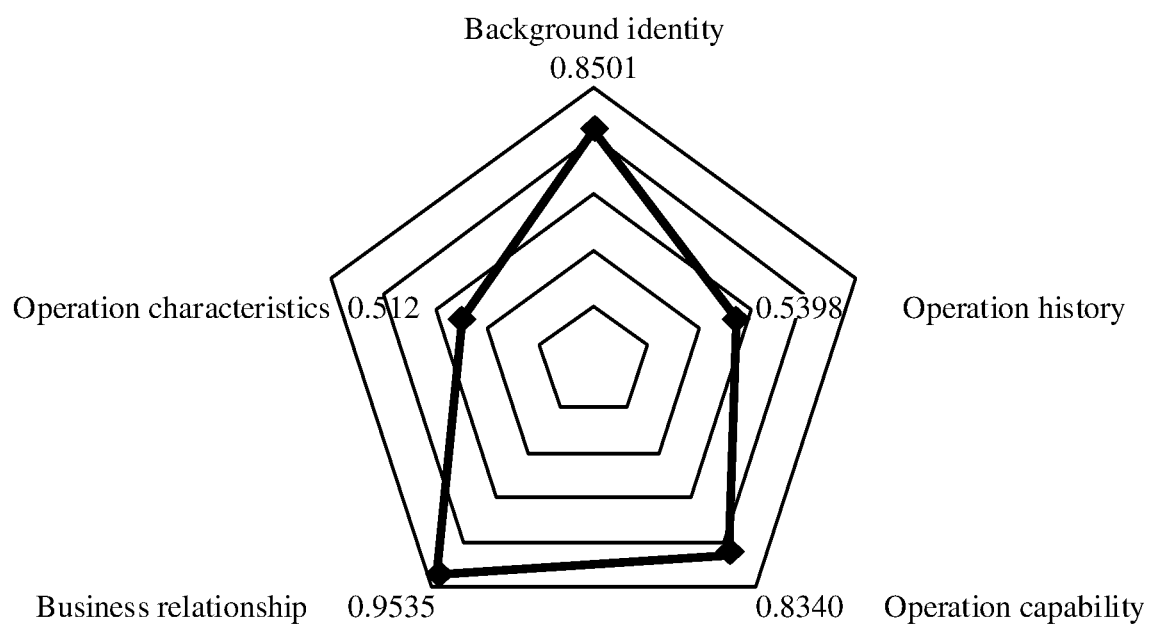
FIG. 3 is a schematic diagram of a merchant health portrait in the merchant evaluation method according to an embodiment.

As to the above-mentioned health portrait and health score (0.7150) obtained through FIG. 3, an all-round evaluation can be comprehensively conducted on the merchant. In this way, not only a health score is provided, but also a health portrait is provided, enabling more intuitive examination of the health status of each evaluation index; and in addition, because the evaluation is conducted based on merchant historical data, data distribution of the merchant to be evaluated among history merchants can be reflected.

It can be seen that, in the merchant evaluation method 200, firstly, by setting evaluation indexes in multiple dimensions, all-round evaluation can be conducted on a merchant to be evaluated; secondly, starting from data analysis, for example, obtaining, by calculation based on standard normal distribution, a health portrait of the merchant to be evaluated and obtaining, by calculation based on a geometric mean, a health score of the merchant to be evaluated. Thus, the driving effect on data is strengthened and the human experience is weakened, making the evaluation results more credible. In addition, by not only providing the health score but also providing the health portrait, the health condition of each evaluation index can be more intuitively viewed, and moreover, because the evaluation is conducted based on the merchant historical data (e.g., black sample and white sample), data distribution of the merchant to be evaluated among history merchants can be reflected, and the health of the merchant can be measured according to the merchant's position in the score distribution.

Figure 4:
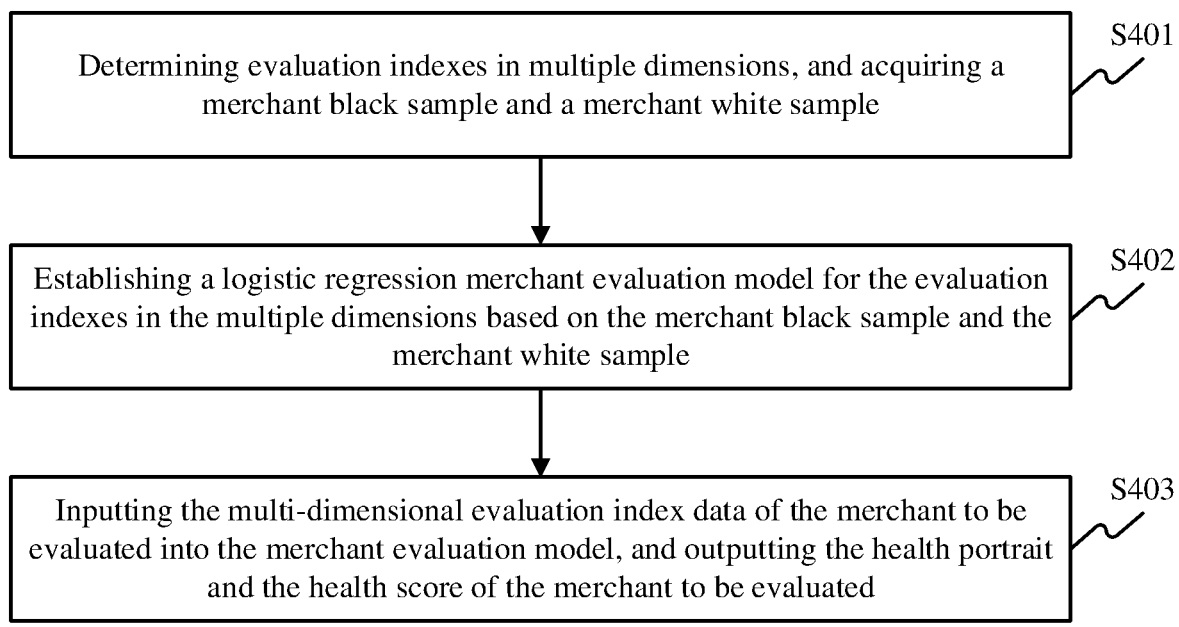
FIG. 4 is a flowchart of a merchant evaluation method according to an embodiment.

FIG. 4 is a flow chart of a merchant evaluation method 400, according to an embodiment. Referring to FIG. 4, the method 400 includes the following steps.

In step S401, evaluation indexes in multiple dimensions are determined, and a merchant black sample and a merchant white sample are acquired.

In the embodiment, a merchant may be an entity unit engaged in sales business and directly facing external customers, such as merchants of Alipay Koubei and merchants of offline Alipay scan pay. For example, a merchant may be a physical store. In order to conduct all-round evaluation on the merchant, multiple evaluation indexes can be set. It can be appreciated that the more evaluation indexes there are, the more reliable the evaluation result of the merchants becomes. In other words, evaluation indexes in multiple dimensions are set, so as to obtain an evaluation result of higher credibility through analysis and processing of the multi-dimensional index data.

In an embodiment, the evaluation indexes in the multiple dimensions may include any combination of merchant background identity, merchant operation history, merchant operation capability, merchant business relationship, and merchant operation characteristics.

In an embodiment, the established merchant evaluation model is supervised. Accordingly, it is necessary to obtain a black sample and a white sample in advance. For example, a merchant who has been cleared and has been complained and verified in history is taken as a black sample, and a mature merchant without a complaint record is taken as a white sample.

In step S402, a logistic regression merchant evaluation model is established for the evaluation indexes in the multiple dimensions based on the merchant black sample and the merchant white sample.

In the embodiment, logistic regression is a generalized linear model and shares many similarities with multiple linear regression analysis. Logistic regression essentially is the probability of occurrence divided by the probability of no occurrence and then the logarithm thereof being taken. This transformation changes the contradiction between value intervals and the curve relationship between a dependent variable and an independent variable. The reason is that the probability of occurrence and the probability of no occurrence become a ratio, and this ratio is a buffer which expands the value range, and then logarithmic transformation is performed, thereby changing the whole dependent variable.

In the embodiment, a logistic regression merchant evaluation model is established for the evaluation indexes in multiple dimensions based on the merchant black sample and the merchant white sample, that is, obtaining a logistic regression model for each evaluation index based on the probability of occurrence of each evaluation index in the merchant black sample and the merchant white sample.

In step S403, the multi-dimensional evaluation index data of the merchant to be evaluated is input into the merchant evaluation model, and the health portrait and the health score of the merchant to be evaluated are output.

In an embodiment, the method 400 can further include: for the multi-dimensional evaluation index data, obtaining, by calculation based on standard normal distribution, a health portrait of the merchant to be evaluated, and obtaining, by calculation based on a geometric mean, a health score of the merchant to be evaluated.

For example, obtaining, by calculation based on standard normal distribution, a health portrait of the merchant to be evaluated includes: inputting the multi-dimensional evaluation index data into the merchant evaluation model, obtaining, by calculation based on standard normal distribution, a probability value of evaluation index data in each dimension, and synthesizing the probability value of the evaluation index data in each dimension to obtain the health portrait of the merchant to be evaluated, wherein the health portrait of the merchant to be evaluated reflects normal distribution of the merchant to be evaluated in merchant evaluation historical data.

Also for example, obtaining, by calculation based on a geometric mean, a health score of the merchant to be evaluated includes: obtaining the health score of the merchant to be evaluated by way of taking an evaluation geometric number of the probability value of the evaluation index data in each dimension of the merchant to be evaluated.

Figure 5:
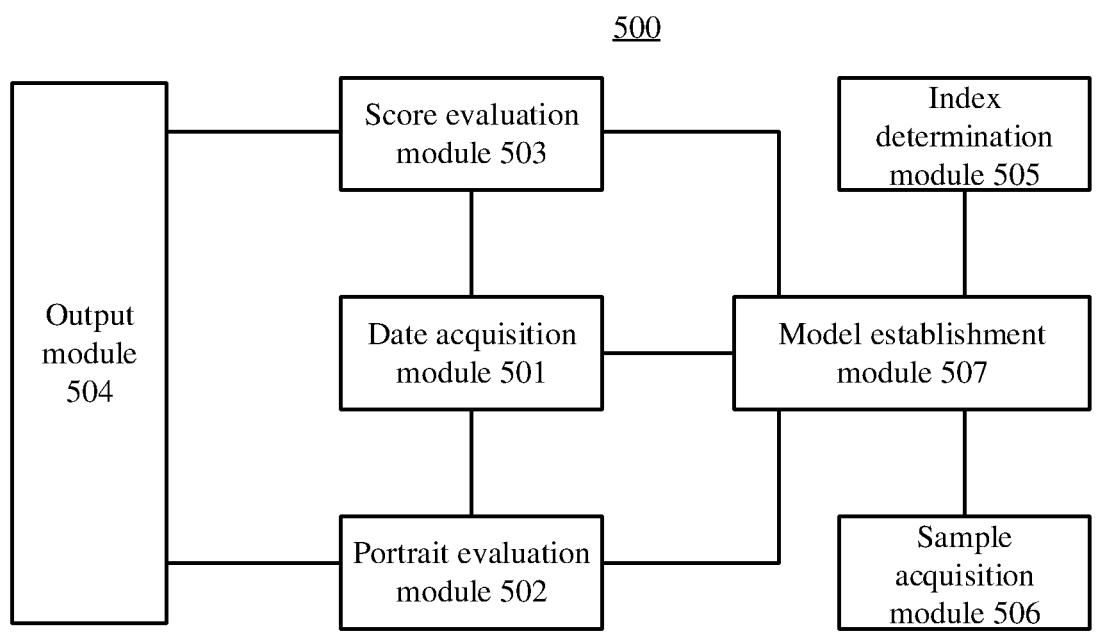
FIG. 5 is a schematic diagram of a merchant evaluation system according to an embodiment.

FIG. 5 is a schematic diagram of a merchant evaluation system 500, according to an embodiment. Referring to FIG. 5, the merchant evaluation system 500 includes: a data acquisition module 501 for acquiring multi-dimensional evaluation index data of a merchant to be evaluated; a portrait evaluation module 502 for obtaining, by calculation based on standard normal distribution, a health portrait of the merchant to be evaluated for the multi-dimensional evaluation index data; a score evaluation module 503 for obtaining, by calculation based on a geometric mean, a health score of the merchant to be evaluated; and an output module 504 for outputting the health portrait and the health score of the merchant to be evaluated.

In an embodiment, the system 500 further includes: an index determination module 505 for determining evaluation indexes in multiple dimensions; a sample acquisition module 506 for acquiring a merchant black sample and a merchant white sample; and a model establishment module 507 for establishing a logistic regression merchant evaluation model for the evaluation indexes in the multiple dimensions based on the merchant black sample and the merchant white sample.

In an embodiment, the portrait evaluation module 502 is used for inputting the multi-dimensional evaluation index data into the merchant evaluation model, obtaining, by calculation based on standard normal distribution, a probability value of evaluation index data in each dimension, and synthesizing the probability value of the evaluation index data in each dimension to obtain the health portrait of the merchant to be evaluated, wherein the health portrait of the merchant to be evaluated reflects normal distribution of the merchant to be evaluated in merchant evaluation historical data.

In an embodiment, the score evaluation module 503 is used for obtaining the health score of the merchant to be evaluated by way of taking an evaluation geometric number of the probability value of the evaluation index data in each dimension of the merchant to be evaluated.

In an embodiment, the multi-dimensional evaluation index data includes any combination of merchant background identity data, merchant operation history data, merchant operation capability data, merchant business relationship data, and merchant operation characteristics data.

Figure 6:
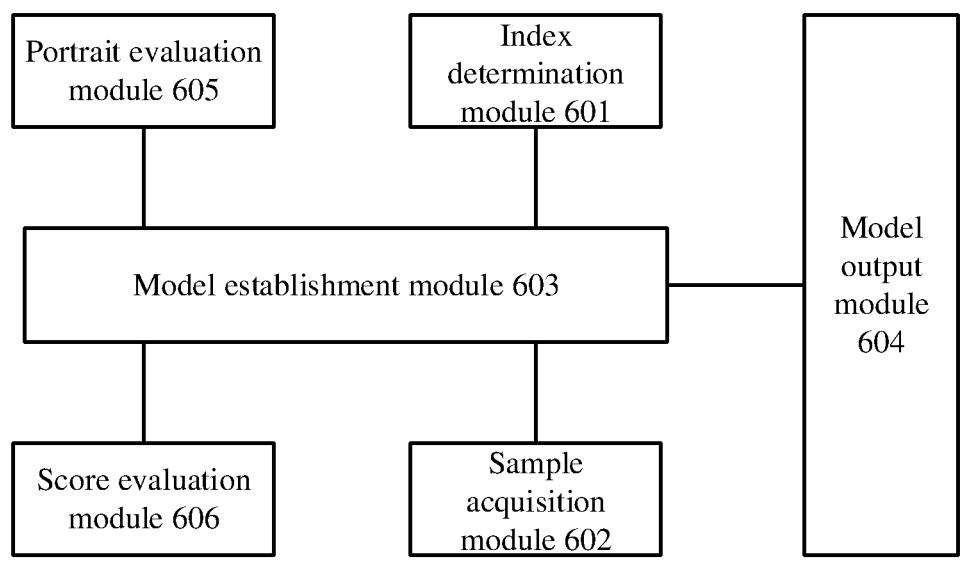
FIG. 6 is a schematic diagram of a merchant evaluation system according to an embodiment.

FIG. 6 is a schematic diagram of a merchant evaluation system 600, according to an embodiment. The merchant evaluation system 600 includes: an index determination module 601 for determining evaluation indexes in multiple dimensions; a sample acquisition module 602 for acquiring a merchant black sample and a merchant white sample; a model establishment module 603 for establishing a logistic regression merchant evaluation model for the evaluation indexes in the multiple dimensions based on the merchant black sample and the merchant white sample; and a model output module 604 for inputting the multi-dimensional evaluation index data of the merchant to be evaluated into the merchant evaluation model, and outputting the health portrait and the health score of the merchant to be evaluated.

In an embodiment, the system 600 further includes: a portrait evaluation module 605 for obtaining, by calculation based on standard normal distribution, a health portrait of the merchant to be evaluated for the multi-dimensional evaluation index data; and a score evaluation module 606 for obtaining, by calculation based on a geometric mean, a health score of the merchant to be evaluated.

In an embodiment, the portrait evaluation module 605 is used for inputting the multi-dimensional evaluation index data into the merchant evaluation model, obtaining, by calculation based on standard normal distribution, a probability value of evaluation index data in each dimension, and synthesizing the probability value of the evaluation index data in each dimension to obtain the health portrait of the merchant to be evaluated, wherein the health portrait of the merchant to be evaluated reflects normal distribution of the merchant to be evaluated in merchant evaluation historical data.

In an embodiment, the score evaluation module 606 is used for obtaining the health score of the merchant to be evaluated by way of taking an evaluation geometric number of the probability value of the evaluation index data in each dimension of the merchant to be evaluated.

In an embodiment, the multi-dimensional evaluation index data includes any combination of merchant background identity data, merchant operation history data, merchant operation capability data, merchant business relationship data, and merchant operation characteristics data.

Figure 7:
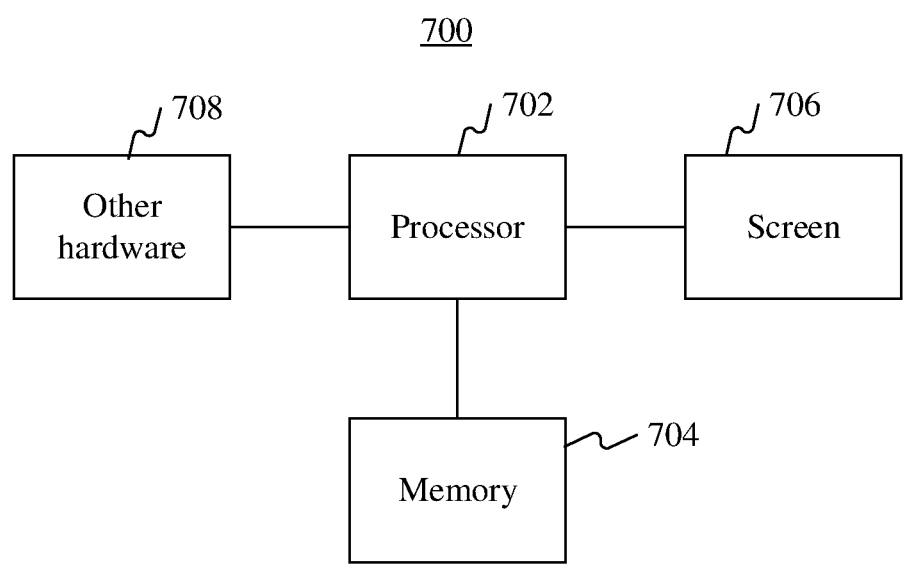
FIG. 7 is a schematic diagram of a merchant evaluation system according to an embodiment.

FIG. 7 is a schematic diagram of a merchant evaluation system 700, according to an embodiment. Referring to FIG. 7, the system 700 may include a processor 702, a memory 704, a screen 706, and other hardware 708, such as a chip for transmitting and receiving wireless signals, a board card for implementing a network communication interface, an input/output interface, etc.

The processor 702 may include one or more dedicated processing units, application-specific integrated circuits (ASICs), field-programmable gate arrays (FPGAs), or various other types of processors or processing units. The processor 702 is coupled with the memory 704 and is configured to execute instructions stored in the memory 704 to perform the above described methods.

The memory 704 may include a non-permanent memory, a random access memory (RAM) and/or a non-volatile memory (such as a read-only memory (ROM) or a flash memory (flash RAM)), etc.

In an embodiment, there is also provided a non-transitory computer-readable storage medium having stored therein computer program instructions that, when executed by a processor of a device, such as the system 700, cause the device to perform the above described merchant evaluation methods.

The specification is described with reference to flowcharts and/or block diagrams of the method, device (system) and computer program product according to the embodiments of the specification. It should be understood that computer program instructions may implement each process and/or block in the flowcharts and/or block diagrams and combinations of processes and/or blocks in the flowcharts and/or block diagrams. These computer program instructions may be provided to a general-purpose computer, a special-purpose computer, an embedded processor, or a processor of other programmable data processing devices to produce a machine, so that an apparatus for implementing a specified function in one or more processes in the flowcharts and/or in one or more blocks in the block diagrams is produced by the instructions executed by the processor of the computer or other programmable data processing devices.

These computer program instructions may also be stored in a computer readable memory that can guide a computer or other programmable data processing devices to operate in a particular manner, such that the instructions stored in the computer readable memory produce a manufactured product, including an instruction device. The instruction device implements a function specified in one or more processes in the flowcharts and/or in one or more blocks in the block diagrams.

These computer program instructions may also be loaded onto a computer or other programmable data processing devices, such that a series of operation steps are performed on the computer or other programmable devices, thus producing computer-implemented processing. Therefore, the instructions executed on the computer or other programmable devices provide steps for implementing a function specified in one or more processes in the flowcharts and/or in one or more blocks in the block diagrams.

Although exemplary embodiments of the specification have been described, those skilled in the art can make other changes and modifications to these embodiments once they learn the basic inventive concept. Therefore, the appended claims are intended to be construed as including the exemplary embodiments and all changes and modifications that fall within the scope of the specification.

Those skilled in the art can make various changes and variations to the exemplary embodiments without departing from the spirit and scope of the specification. In this way, if these modifications and variations of the specification fall within the scope of the claims of the specification and the equivalent technologies thereof, the specification is also intended to include these modifications and variations.

The invention claimed is:

1. A merchant evaluation method, comprising:
acquiring, by a processor, a merchant black sample and a merchant white sample of a plurality of merchants, wherein the merchant black sample includes a merchant receiving negative user feedback, and the merchant white sample includes a merchant receiving positive user feedback;

establishing, by the processor, a merchant evaluation model for evaluation indexes in multiple dimensions based on the merchant black sample and the merchant white sample, wherein the merchant evaluation model is established based on supervised regression modeling;

acquiring, by the processor, multi-dimensional evaluation index data of a first merchant to be evaluated, wherein the multi-dimensional evaluation index data comprises any combination of merchant background identity evaluation index data, merchant operation history evaluation index data, merchant operation capability evaluation index data, merchant business relationship evaluation index data, and merchant operation characteristics evaluation index data;

obtaining, by the processor, a health portrait and a health score of the first merchant to be evaluated using the merchant evaluation model, wherein obtaining the health portrait comprises: inputting the multi-dimensional evaluation index data into the merchant evaluation model; and obtaining, by the merchant evaluation model using calculation based on standard normal distribution, a probability value of evaluation index data in each dimension of the multiple dimensions, and wherein obtaining the health score comprises: determining a comprehensive score based on probability values of evaluation index data in all dimensions of the multiple dimensions, by calculating a geometric mean of the probability values of the evaluation index data in all dimensions of the multiple dimensions;

receiving, by the processor, a request for the health portrait and the health score of the first merchant for e-commerce shopping from a user; and in response to the request, displaying, by the processor on a screen, the health portrait and the health score of the first merchant, wherein displaying the health portrait comprises presenting a chart with the evaluation indexes of the multiple dimensions associated with the merchant evaluation model and the probability value of the evaluation index data in each dimension of the multiple dimensions, and wherein displaying the health score comprises displaying the determined comprehensive score.

2. The method according to claim 1, wherein establishing, by the processor, a merchant evaluation model comprises:
establishing a logistic regression model as the merchant evaluation model.

3. The method according to claim 1, wherein obtaining the health portrait of the first merchant to be evaluated comprises:
synthesizing the probability value of the evaluation index data in each dimension to obtain the health portrait of the first merchant to be evaluated, wherein the health portrait of the first merchant to be evaluated reflects normal distribution of the first merchant to be evaluated in merchant evaluation historical data.

4. The method according to claim 1, further comprising:
obtaining the evaluation index data in each dimension from original evaluation index description information, wherein the original evaluation index description information is inputted into an index model preset for an index to obtain evaluation index data used for describing a score of the index.

5. A merchant evaluation system, comprising:
a processor; and
a memory storing instructions that, when executed by the processor, cause the processor to perform:

acquiring a merchant black sample and a merchant white sample of a plurality of merchants, wherein the merchant black sample includes a merchant receiving negative user feedback, and the merchant white sample includes a merchant receiving positive user feedback;

establishing a merchant evaluation model for evaluation indexes in multiple dimensions based on the merchant black sample and the merchant white sample, wherein the merchant evaluation model is established based on supervised regression modeling;

acquiring multi-dimensional evaluation index data of a first merchant to be evaluated, wherein the multi-dimensional evaluation index data comprises any combination of merchant background identity evaluation index data, merchant operation history evaluation index data, merchant operation capability evaluation index data, merchant business relationship evaluation index data, and merchant operation characteristics evaluation index data;

obtaining a health portrait and a health score of the first merchant to be evaluated using the merchant evaluation model, wherein obtaining the health portrait comprises: inputting the multi-dimensional evaluation index data into the merchant evaluation model; and obtaining, by the merchant evaluation model using calculation based on standard normal distribution, a probability value of evaluation index data in each dimension of the multiple dimensions, and wherein obtaining the health score comprises: determining a comprehensive score based on probability values of evaluation index data in all dimensions of the multiple dimensions, by calculating a geometric mean of the probability values of the evaluation index data in all dimensions of the multiple dimensions;

receiving a request for the health portrait and the health score of the first merchant for e-commerce shopping from a user; and in response to the request, displaying, on a screen, the health portrait and the health score of the first merchant, wherein displaying the health portrait comprises presenting a chart with the evaluation indexes of the multiple dimensions associated with the merchant evaluation model and the probability value of the evaluation index data in each dimension of the multiple dimensions, and wherein displaying the health score comprises displaying the determined comprehensive score.

6. The system according to claim 5, wherein establishing the merchant evaluation model comprises:
establishing a logistic regression model as the merchant evaluation model.

7. The system according to claim 5, the memory storing the instructions that, when executed by the processor, cause the processor to further perform:
synthesizing the probability value of the evaluation index data in each dimension to obtain the health portrait of the first merchant to be evaluated, wherein the health portrait of the first merchant to be evaluated reflects normal distribution of the first merchant to be evaluated in merchant evaluation historical data.

8. The system according to claim 5, wherein the evaluation index data in each dimension is obtained from original evaluation index description information, wherein the original evaluation index description information is inputted into an index model preset for an index to obtain evaluation index data used for describing a score of the index.

9. A non-transitory computer-readable storage medium having stored therein instructions that, when executed by a processor of a device, cause the device to perform a merchant evaluation method, the method comprising:

acquiring a merchant black sample and a merchant white sample of a plurality of merchants, wherein the merchant black sample includes a merchant receiving negative user feedback, and the merchant white sample includes a merchant receiving positive user feedback;

establishing a merchant evaluation model for evaluation indexes in multiple dimensions based on the merchant black sample and the merchant white sample, wherein the merchant evaluation model is established based on supervised regression modeling;

acquiring multi-dimensional evaluation index data of a first merchant to be evaluated, wherein the multi-dimensional evaluation index data comprises any combination of merchant background identity evaluation index data, merchant operation history evaluation index data, merchant operation capability evaluation index data, merchant business relationship evaluation index data, and merchant operation characteristics evaluation index data;

obtaining a health portrait and a health score of the first merchant to be evaluated using the merchant evaluation model, wherein obtaining the health portrait comprises:

inputting the multi-dimensional evaluation index data into the merchant evaluation model; and obtaining, by the merchant evaluation model using calculation based on standard normal distribution, a probability value of evaluation index data in each dimension of the multiple dimensions, and wherein obtaining the health score comprises: determining a comprehensive score based on probability values of evaluation index data in all dimensions of the multiple dimensions, by calculating a geometric mean of the probability values of the evaluation index data in all dimensions of the multiple dimensions receiving a request for the health portrait and the health score of the first merchant for e-commerce shopping from a user; and in response to the request, displaying, on a screen, the health portrait and the health score of the first merchant, wherein displaying the health portrait comprises presenting a chart with the evaluation indexes of the multiple dimensions associated with the merchant evaluation model and the probability value of the evaluation index data in each dimension of the multiple dimensions, and wherein displaying the health score comprises displaying the determined comprehensive score.

* * * * *